United States Patent [19]

Gupta et al.

[11] 4,433,173

[45] Feb. 21, 1984

[54] ACETOPHENONE PURIFICATION

[75] Inventors: Vijai P. Gupta, Berwyn; Frank W. Melpolder, Wallingford; Walter A. Mameniskis, Drexel Hill, all of Pa.

[73] Assignee: Atlantic Richfield Company, Los Angeles, Calif.

[21] Appl. No.: 384,317

[22] Filed: Jun. 2, 1982

[51] Int. Cl.$^3$ .............................................. C07C 45/83
[52] U.S. Cl. ...................................... 568/324; 203/64
[58] Field of Search ........................... 203/64; 568/324

[56]  References Cited

U.S. PATENT DOCUMENTS

| | | | |
|---|---|---|---|
| 2,444,893 | 7/1948 | Lake | 203/64 |
| 2,894,047 | 7/1959 | Uitti | 203/64 |
| 3,105,018 | 9/1963 | Freure | 203/64 |
| 3,310,478 | 3/1967 | Amir | 203/64 |
| 4,229,262 | 10/1980 | Reed et al. | 203/64 |

*Primary Examiner*—James H. Reamer
*Attorney, Agent, or Firm*—Craig E. Larson

[57] ABSTRACT

Purification of acetophenone containing difficultly separable impurities by extractive distillation with a solvent selected from the group consisting of oligomers of 1,2-glycols, said oligomers having from 4 to 9 carbon atoms per molecule.

9 Claims, No Drawings

ACETOPHENONE PURIFICATION

BACKGROUND OF THE INVENTION

The present invention relates to the purification of aromatic ketones. More particularly, the present invention relates to the purification of acetophenone containing difficultly separable hydrocarbon impurities.

Acetophenone is a by-product of various known processes for the preparation of styrene by the dehydration of alpha-methylbenzyl alcohol, when ethylbenzene is employed as the alcohol precursor. Such dehydration processes are exemplified by the liquid phase aralkanol dehydration process disclosed in U.S. Pat. No. 3,526,674. The net product from the reaction system disclosed in the '674 Patent comprises styrene, acetophenone and alpha-methyl-benzyl alcohol and minor amounts of other impurities (e.g., see Example VI of the '674 Patent). Styrene product is separable from this net reaction system product by fractional distillation, as is a by-product comprising alpha-methylbenzyl alcohol and acetophenone. The acetophenone content of this by-product stream may range broadly from about 30 to 80 wt. %.

By subjecting the by-product to catalytic hydrogenation, acetophenone may be converted to alpha-methylbenzyl alcohol and the hydrogenate may be returned to the dehydration zone to produce additional styrene product. For example, see U.S. Pat. No. 3,927,120.

Acetophenone by-product streams would also appear to be a valuable source of high-purity (98 wt. %+) acetophenone product. For example, light impurities such as styrene, alpha-methylstyrene, cumene, benzaldehyde and ethylbenzene could be removed overhead in a first fractional distillation and heavy impurities, including alpha-methylbenzyl alcohol could be removed in the bottoms of a second fractional distillation. However, it has been found that such fractional distillation of acetophenone by-product streams recovered from liquid phase dehydration processes operating according to the teachings of the '674 patent yield a final product containing only about 97 wt. % acetophenone.

The known impurities which were the keys in the design of the conventional separation scheme—benzaldehyde (light key) and alpha-methylbenzyl alcohol (heavy key)—were completely separated. However, the presence of certain other (previously unknown) impurities makes it impracticable to obtain better than 97 wt. % purity acteophenone by the two conventional distillation steps. The previously unknown impurities have been identified as 1,2,4-trimethylbenzene; 1-methyl tetralin; an alkylated benzyl alcohol (164 molecular weight); and paraffinic hydrocarbons (156 average molecular weight).

U.S. Pat. No. 3,819,492 discloses the purification of aromatic ketones containing difficulty separable acids and alcohols by distillation in the presence of an acid capable of catalyzing esterification between the acid and alcohol impurities. Such impurities are then separable by conventional distillation.

An object of the present invention is a method for the purification of acetophenone containing difficulty separable hydrocarbon impurities. A related object is the recovery of high-purity acetophenone from byproduct streams produced in the production of styrene by the dehydration of alpha-methylbenzyl alcohol, especially byproduct streams produced in liquid-phase dehydration processes.

SUMMARY OF THE INVENTION

It has now been found that difficulty separable impurities may be separated to produce high-purity acetophenone by extractive distillation with a particular class of distillation solvents. The distillation solvents employed in the process of this invention are selected from the group consisting of oligomers of 1,2-glycols, said oligomers having from 4 to 9, preferably from 4–6, carbon atoms per molecule. The presently preferred distillation solvents are diethylene glycol, triethylene glycol and dipropylene glycol.

DETAILED DESCRIPTION OF THE INVENTION

Acetophenone containing difficultly separable impurities, to be purified by the method of this invention, may be obtained from a wide variety of processes: the oxidation of ethylbenzene may form methylbenzyl alcohol, acetophenone, benzoic acid and other organic residues (U.S. Pat. No. 3,040,101); the oxidation of ethylbenzene to form ethylbenzene hydroperoxide also results in the formation of acetophenone as a byproduct; decomposition of ethylbenzene hydroperoxide forms acetophenone as a primary product; the reaction of olefins with ethylbenzene hydroperoxide may result in the formation of acetophenone (see U.S. Pat. No. 4,308,409).

Although not limited thereto, the process of this invention is especially applicable to the purification of acetophenone obtained from processes wherein ethylbenzene hydroperoxide is present, either as a reactant or as an intermediate.

This invention finds its greatest applicability in the recovery of high-purity acetophenone from byproduct mixtures formed in the simultaneous production of oxirane compounds and α-methylbenzyl alcohol, wherein α-methylbenzyl alcohol is a product of the reaction of ethylbenzene hydroperoxide and an olefin, and ethylbenzene hydroperoxide is formed by the oxidation of ethylbenzene. See U.S. Pat. Nos. 3,350,422 and 3,351,635. As noted, acetophenone is formed in both the ethylbenzene oxidation zone, and the ethylbenzene hydroperoxide/olefin reaction zones of such processes.

In a specific embodiment of this invention, acetophenone containing difficultly separable impurities is derived from byproduct mixtures resulting from the dehydration of alpha-methylbenzyl alcohol to form styrene, particularly from byproduct mixtures resulting from liquid phase dehydration of alpha-methylbenzyl alcohol according to U.S. Pat. No. 3,526,674. Such byproduct mixtures contain acetophenone formed in preceding ethylbenzene oxidation and ethylbenzene hydroperoxide/olefin reaction zones, as described above.

Such product mixtures have been discovered to contain impurities which are impractical to remove by conventional distillation procedures. Analytical evidence suggests the particular impurities to be those identified in Table I below, which also shows the volatilities of these impurities relative to acetophenone.

TABLE I

| Impurity | Volatility Relative to Actephenone (at about 120° C., 70 mmHg) |
|---|---|
| Paraffin hydrocarbons (156 ave. mol. wt.) | 1.025 |

TABLE I-continued

| Impurity | Volatility Relative to Actephenone (at about 120° C., 70 mmHg) |
|---|---|
| 1,2,4-Triethylbenzene | 1.006 |
| Alkylated Benzyl Alcohol (164 mol. wt.) | 0.974 |
| 1-Methyltetralin | 0.986 |

By the term "difficultly separable impurities" is meant impurities such as those exemplified by the impurities shown in Table I. Thus, the impurities may be alkyl, alkyl aromatic, alkylated benzyl alcohol, or hydroaromatic compounds having volatilities relative to acetophenone within the range from about 0.9 to 1.1. Excluded from this definition are compounds such as alpha-methylbenzyl alcohol which has a volatility relative to acetophenone of about 0.7.

In a specific embodiment of the present invention, high-purity acetophenone is produced from the product of liquid phase dehydration of alpha-methylbenzyl alcohol by recovering a crude styrene monomer product stream overhead in a first distillation of the dehydration zone effluent, passing the bottoms stream from the crude styrene monomer recovery zone to a second distillation zone for the separation of less difficultly separable, higher boiling impurities (heavier than acetophenone), and finally subjecting the second distillation zone overhead to solvent extractive distillation according to the method of this invention. Acetophenone purities in excess of 99 wt. % are readily obtained by applying the process of this invention to such a feedstream.

Other separation schemes will be apparent to one skilled in the art and are within the scope of this invention. For example, the second distillation zone overhead may be subjected to an intermediate distillation step for the separation of less difficultly separable, lower-boiling impurities (lighter than acetophenone) and the intermediate distillation zone bottoms may then be subjected to solvent extractive distillation according to the method of this invention.

In extractive distillation, the distillation solvent should be considerably less volatile than the regular feed components and is added near the top of the column. Because of its low volatility, the agent behaves as a typical heavier-than-heavy key component and is also readily separable from the product streams. The solvent selected for an extractive distillation should have a boiling point sufficiently higher than the feed component so that separation of the solvent from the bottoms is easily accomplished.

A mixture consisting essentially of acetophenone and solvent is withdrawn as bottoms from the extractive distillation zone of this invention. Solvent comprising oligomers of lower 1,2-glycols are readily separable from acetophenone in a subsequent solvent recovery distillation zone. It has been found that although other solvents, such as monopropylene glycol, may be effective distillation agents for separating difficultly separable impurities from acetophenone, the separation of such other solvents—esp. lower glycol solvents—from acetophenone is extremely difficult because of the strong tendency of lower glycols to azeotrope with acetophenone.

Selection of operating conditions to be employed in the extractive distillation is within the skill of the art, given a particular acetophenone feedstream and the relative volatility of the solvent employed. Typically, the extractive distillation column would be operated under subatmospheric pressure, within the range from about 10 to 500 mm Hg. Pressures in excess of 500 mm Hg reduce the volatility of the difficultly separable impurities relative to acetophenone and are not preferred.

In the process of this invention, acetophenone containing difficultly separable impurities is distilled through a distillation apparatus (e.g., a distillation column) having at least 10 theoretical plates of separation.

Preferably the distillation process of the invention is conducted at a reflux ratio (L/D) of between about 1:1 and about 20:1. Typically, a reflux ratio of about 5:1 to 15:1 is employed.

The solvent-addition rate can vary considerably. Increased rates increase the solvent concentration in the column and, therefore, improve selectivity and reduce tray requirements. However, this desirable effect of increasing solvent-addition rate must be balanced against the resulting, increased heat requirements and larger cross-section of the extractive column and the larger size of the solvent recovery column. Usually, the weight ratio of solvent to acetophenone feed is between about 0.1:1 to about 8:1, preferably between about 0.5:1 to 2:1.

The following examples set forth embodiments of the present invention. It should be understood that these examples are illustrative rather than limiting.

In the examples relative volatilities and related parameters are expressed as follows:

$$\alpha_{a-b} = \frac{Y_a/Y_b}{X_a/X_b}$$

where
$\alpha$ a-b = relative volatility of a compound to b
$Y_a$ = vapor composition of a (mole %)
$Y_b$ = vapor composition of b (mole %)
$X_a$ = liquid composition of a (mole %)
$X_b$ = liquid composition of b (mole %)

COMPARATIVE EXAMPLE 1

This comparative Example demonstrates the impracticability of producing high purity acetophenone by straight fractional distillation of an acetophenone by-product stream recovered in the process for the dehydration of alpha-methylbenzyl alcohol to form styrene, as described above. Major components of the by-product stream were acetophenone (49.5 wt. %) and alpha-methylbenzyl alcohol (31.0 wt. %). Other components present in minor amounts were ethylbenzene (2.4 wt. %), styrene (1.2 wt. %), benzaldehyde (1.2 wt. %), 1,2,4-triethylbenzene (1.4 wt. %) and 1-methyl tetralin (1.2 wt. %).

This feed stock was distilled in two stages. Lights (20% of feed) were taken overhead in a first stage which comprised a 55-tray column with 35 stripping trays operated at a reflux ratio of 10:1, an overhead pressure of 20 mm Hg, an overhead temperature of 105° C. and a reboiler temperature of 131° C. The bottom stream from the lights column was then fed to the second stage—a heavies column which comprised an 80-tray, 2 inch diameter Oldershaw column with 50 rectifying trays. The heavies column was run at a reflux ratio of 10:1, an overhead pressure of 20 mm Hg, an overhead temperature of 120° C. and a reboiler temperature of 141° C.

The acetophenone product recovered overhead in the heavies column contained only about 96 wt. % acetophenone. Major impurities in the acetophenone product were subsequently identified as described above.

A sample of the heavies column distillate was washed with water and (separately) with an aqueous solution of calcium chloride. Neither of these treatments was found to effect any improvement in product composition.

EXAMPLES 1–2 AND COMPARATIVE EXAMPLES 2–4

Vapor-liquid equilibrium data were obtained in an Othmer still for equal-weight mixtures of various solvents with an acetophenone byproduct stream (95 wt. %) obtained by the two stage distillation method described in Comparative Example 1. The still temperatures and pressures and the volatilities of components present in the mixture relative to the acetophenone are shown in Table II below.

TABLE II

| | Solvent | Temp. (°C.) | Press. (mm Hg) | Paraffin[d] | TEB[a] | Benzyl Alcohol[b] | 1-Me Tetralin[c] | Solvent |
|---|---|---|---|---|---|---|---|---|
| Comp. Ex. | | | | | | | | |
| 2 | Dodecane | 125 | 73 | N.A. | 0.855 | 0.947 | 0.923 | 0.954 |
| 3 | Dodecylbenzene | 135 | 75 | 0.990 | 0.826 | 0.918 | 0.815 | 0.257 |
| 4 | Monopropylene glycol | 117 | 75 | 2.71 | 1.95 | 1.46 | 1.63 | 0.751 |
| Example | | | | | | | | |
| 1 | Dipropylene glycol | 133 | 75 | 1.70 | 1.41 | 1.21 | 1.30 | 0.181 |
| 2 | Diethylene glycol | 132 | 74 | 3.87 | 2.22 | 1.83 | 1.61 | 0.100 |

[a]1,2,4-Triethylbenzene
[b]Alkylated benzyl alcohol (164 mol. wt.)
[c]1-Methyl Tetralin
[d]Paraffin hydrocarbons (156 ave. mol. wt.)

Addition to equal weights of hydrocarbon solvents (comparative examples 2 and 3) slightly enhanced the volatility of acetophenone, but separation would still very difficult. However, addition of glycol-type solvents (comparative example 4 and examples 1–2) was found to dramatically enhance the volatilities of impurities relative to acetophenone. Although monopropylene glycol (comparative example 4) increases the volatilities of the impurities relative to acetophenone, subsequent separation of high-purity acetophenone from the extractive distillation column bottoms is impractical because of glycol/acetophenone azeotrope formation in the solvent recovery zone.

Solvents comprising oligomers of lower, 1,2 glycols, however, are easily separable from acetophenone, and high-purity acetophenone is recovered overhead in the solvent recovery zone.

What is claimed is:

1. A process for the purification of acetophenone from mixtures containing difficulty separable impurities consisting essentially of alkyl, alkyl aromatic, alkylated benzyl alcohol or hydroaromatic compounds having volatilies relative to acetophenone within the range from about 0.9 to 1.1 which process comprises extractive distillation of the mixture with an added solvent selected from the group consisting of oligomers of 1,2-glycols, said oligomers having from 4 to 9 carbon atoms per molecule, and recovering high-purity acetophenone from the bottoms stream of said extractive distillation.

2. The process of claim 1 wherein the acetophenone mixture containing difficultly separable impurities is obtained from processes wherein ethylbenzene hydroperoxide is present.

3. The process of claim 2 wherein the said mixture is obtained from processes comprising oxidation of ethylbenzene to form ethylbenzene hydroperoxide.

4. The process of claim 2 wherein the said mixture is obtained from processes comprising reaction of ethylbenzene hydroperoxide and an olefin to form an olefin oxide and alpha-methylbenzyl alcohol.

5. The process of claim 4 wherein the said mixture is obtained from processes comprising dehydration of the alpha-methylbenzyl alcohol to form styrene.

6. The process of claim 1 wherein the said oligomer has from 4 to 6 carbon atoms per molecule.

7. The process of claim 6 wherein the extractive distillation solvent is dipropylene glycol.

8. The process of claim 6 wherein the extractive distillation solvent is diethylene glycol.

9. The process of claim 6 wherein the extractive distillation solvent is triethylene glycol.

* * * * *